United States Patent [19]
Godiard et al.

[11] Patent Number: 5,552,527
[45] Date of Patent: Sep. 3, 1996

[54] HYPER-SENSITIVITY RELATED GENE

[75] Inventors: Laurence Godiard, Köln, Germany; Yves Marco, Castanet-Tolosan, France; Dominique Pontier; Dominique Roby, both of Toulouse, France

[73] Assignee: Sandoz Ltd., Basel, Switzerland

[21] Appl. No.: 446,923

[22] Filed: May 18, 1995

Related U.S. Application Data

[62] Division of Ser. No. 202,054, Feb. 23, 1994.

[30] Foreign Application Priority Data

Feb. 24, 1993 [EP] European Pat. Off. .............. 93102887

[51] Int. Cl.$^6$ .................. C07K 14/415; C12N 15/29; C12N 15/82
[52] U.S. Cl. ................... 530/379; 530/370; 530/377; 536/23.6; 800/205; 435/172.3
[58] Field of Search ................... 530/370, 379, 530/377; 536/23.6; 435/172.3

[56] References Cited

U.S. PATENT DOCUMENTS 5,057,422 10/1991 Bol et al. ............................. 435/240.4
5,312,912 5/1994 Hadwiger et al. ..................... 536/24.1

FOREIGN PATENT DOCUMENTS 3-290190 12/1991 Japan.

OTHER PUBLICATIONS

Marco et al 1990 Plant Molec Biol 15: 145–154.
Jaeck et al 1992 Molec Plant Microbe Interaction 5(4): 294–300.
Smart et al 1987 Virology 158: 461–464.
Keen 1992 Plant Molec Biol 19: 109–122.
Lindgren et al 1988 Mol Gen Genet 211: 499–506.
Collinge et al 1987 Plant Molec Biol 9: 389–410.
Lamb et al 1992 Bio/Technology 10: 1436–1445.
Pontier et al 1994 (Apr.) The Plant Journal 5(4):507–521.

*Primary Examiner*—Patricia R. Moody
*Attorney, Agent, or Firm*—Lynn Marcus-Wyner

[57] ABSTRACT

The hsr203J gene of SEQ ID No. 1 and individual components thereof including its promoter and regulatory regions thereof, its coding region, its gene product; modifications thereto; applications of said gene, promoter region, regulatory region and coding region and modifications thereto; DNA constructs, vectors and transformed plants each comprising the gene or part thereof.

7 Claims, 10 Drawing Sheets

...TTT GCC AAA ATG GTT CAT GAA AAG CAA GTG ATA GAG

GAA GTA TCC GGC TGG CTT AGA GTT TTC GGG GTA GGT CAG

TCC CTT ATG TTA CGT CCT...

FIG. 1B

HYPER-SENSITIVITY RELATED GENE

This is a Divisional of application Ser. No. 08/202,054, filed on Feb. 23, 1994.

BACKGROUND OF THE INVENTION

This invention relates to an hsr (hypersensitivity-related) gene family and individual components thereof including its promoter and regulatory regions thereof, its coding region, its gene product; modifications thereto; applications of said gene, promoter region, regulatory region and coding region and modifications thereto; DNA constructs, vectors and transformed plants each comprising the gene or part thereof.

The hypersensitive reaction (HR) of higher plants is a local inducible response associated with disease resistance to a pathogen. This response is characterized by a rapid and localized necrosis of tissues invaded by an incompatible (avirulent or non-host) pathogen, which prevents further spread of the invading microorganism. Several defense genes whose products may intervene in this plant response have been extensively studied: they include enzymes of the phenylpropanoid pathway involved in the synthesis of antimicrobial phytoalexins, enzymes with hydrolyric activities, toxic compounds and cell wall proteins. In infected plants, these genes are induced around the necrosis, once it has developed, i.e. late during the HR. Moreover, most of them are also strongly expressed during compatible interactions leading to the disease of the plant, and for some of them, during the normal development of the plant. The lack of specificity of these defense genes as well as their activation in the late steps of the HR suggest that they may not account by itself for establishment of the complex inducible response that is the HR, but rather may accompany this reaction. To date, the molecular mechanisms leading from plant-pathogen recognition to development of the HR are not known. In the "gene for gene" hypothesis, the initial step of plant-pathogen recognition leading to resistance involves the putative interaction between the products of a plant resistance gene and of the corresponding pathogen avirulent gene. Genetic studies indeed revealed that the outcome of many plant-pathogen interactions are determined through single dominant genes in both partners. Several rapid physiological changes have been also associated with the HR, such as electrolyte leakage, changes in respiration rates and more recently oxidative cross-linking of cell-wall proteins. However, in no case has a plant gene been described whose activation is specific or at least preferential during the resistance reaction, and precedes the development of the HR.

It is known that *Pseudomonas solanacearum*, a vascular bacterium, causes a lethal wilting of different plant species including Solanaceae. In this bacterium, a hypersensitive response (hrp) and pathogenicity gene cluster has been shown to control both the ability to elicit the HR on non-host plants and to cause the disease on host plants. In particular, hrp gene routants of *P. solanacearum* have lost the ability to elicit an HR on tobacco plants. Recently, it was established that the hrpN gene of the hrp gene cluster of another bacterial pathogen, *Erwinia amylovora*, encodes a proteinaceous HR elicitor called harpin. This result confirms the important role of hrp genes in eliciting the HR. Upon infiltration of tobacco leaves by an HR-inducing incompatible isolate, six different gene families were characterized which are activated early during the interaction, before any necrosis of the leaf was detected. These genes which were not induced upon infiltration by an hrp-isolate differed by the accumulation levels of their transcripts during the incompatible versus the compatible interactions: the str (sensitivity-related) genes are expressed to a similar extent in both types of interactions, whereas the hsr genes are activated preferentially during the HR.

SUMMARY OF THE INVENTION

The present invention relates to an hsr gene family represented by a gene, hereinafter designated hsr203J, the sequence of which is depicted in SEQ ID No: 1. The putative protein product (SEQ ID No: 2) of the gene exhibits little, if any substantial homology with known proteins. Tests employing i.a. the promoter region of the hsr203J structural gene operably linked to a reporter gene in transient gene expression assays and in transgenic plants indicate that the expression of the hsr203J gene is closely related to the development of hypersensitivity: the promoter is specifically activated during the HR several hours before the appearance of the necrosis, and the localization of its activation is restricted to cells inoculated with an incompatible bacterial isolate.

According to the present invention there is provided a recombinant DNA sequence including a region comprising the nucleotide sequence depicted in SEQ ID No: 1 or a functional equivalent thereof, or a recombinant sequence comprising a part of said region or said equivalent.

BRIEF DESCRIPTION OF THE DRAWINGS

FIG. 1(B) shows the sequence (SEQ ID No: 2) of the pHG21 translation fusion joint. The hsr203J gene sequence is in bold type and the uidA sequence is in standard type. The orientation is 5' to 3', and the arrow indicates the position of the fusion between the sequences.

DETAILED DESCRIPTION OF THE INVENTION

Figure 1A:
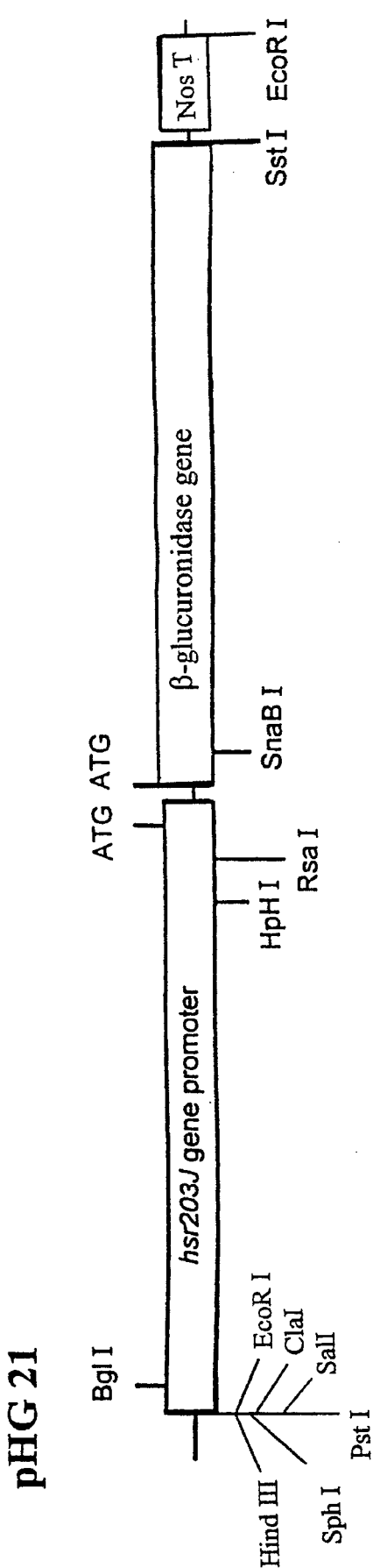
FIG. 1(A) shows a chimeric construct used for transient gene expression assays in tobacco protoplasts and the transformation of tobacco plants via *Agrobacterium tumefaciens*. Specifically the restriction map of the chimeric β-glucuronidase gene on pHG21 (or pHG21A) is depicted. The gene consists of a transitional fusion between 1.4 kb of the 5' flanking sequence from the hsr203J gene and the coding region of the uidA gene linked to the nopaline synthase gene polyadenylation signal (nosT).

Hereinafter where the term "functional equivalent" is used in respect of the protein encoding region of the DNA sequence the term means the said region wherein one or more codons have been replaced by their synonyms, ie codons which specify a corresponding amino acid or a corresponding transcription termination signal.

Where the term "functional equivalent" is used in respect of transcriptional regulatory regions of the sequence the term means the said region wherein one or more nucleotides have been replaced by different nucleotides and/or the region wherein one or more nucleotides have been added or removed with the proviso that the thus produced equivalents retain transcriptional regulatory activity and exhibit substantial homology with the region, or part thereof, which is 5' to the above mentioned protein encoding region.

As used herein, the term "substantial homology" refers to a DNA sequence which hybridizes under conventional hybridization conditions with a reference sequence. Preferably the hybridization conditions refer to hybridization in which the TM value is between 35° and 45° C. Most preferably the term substantial homology refers to a DNA sequence which hybridizes with the reference sequence under stringent conditions (as defined below).

The term "regulatory region" as used herein refers to the nucleotide region in the sequence depicted in SEQ ID No: 1 which is 5' to the protein encoding region in the sequence. The regulatory region thus includes the promoter of the hsr203J gene and the functional components of the promoter which affect transcription. Such functional components include a "deletion promoter" and transcriptional "silencers" and "enhancers".

A "deletion promoter" within the context of the present invention is any hsr203J derived promoter which has a deletion relative to the natural promoter and which still retains promoter activity. Such promoter activity may be enhanced or substantially the same when compared to the native promoter. The skilled man is aware of the manner in which deletion promoters can be assayed for retention of their promoter activity. Deletion promoters according to the present invention are inducible, inter alia, by plant pathogens, and find utility in constructs comprising structural genes providing for improved disease resistance.

Where the term "functional equivalent" is used in connection with a protein, the sequence of which is dictated by at least a part of the DNA sequence depicted in SEQ ID No: 1, the term means a protein having a like function and like or improved specific activity, and a similar amino acid sequence. The present invention includes pure proteins which have an amino acid sequence which is at least 60% similar to the sequence or part (see below) thereof of the protein depicted in SEQ ID No: 2. It is preferred that the degree of similarity is at least 60%, more preferred that the degree of similarity is at least 70% and still more preferred that the degree of similarity is at least 80%.

In the context of the present invention, two amino acid sequences with at least 60% similarity to each other are defined by having at least 70% identical or similar amino acids residues in the same position when aligned optimally allowing for up to 4 deletions or up to 10 additions. For the purpose of the present invention:

Alanine, Serine and Threonine are similar;,

Glutamic acid and Aspartic acid are similar;

Asparagine and Glutamine are similar;,

Arginine and Lysine are similar;,

Isoleucine, Leucine, Methionine and Valine are similar,

Phenylalanine, Tyrosine and Tryptophan are similar.

Where the term "part" is used in connection with a protein sequence, the term means a peptide comprised by the sequence depicted in SEQ ID No: 2 and having at least 5 amino acids. More preferably the peptide has at least 20 amino acids, and still more preferably the peptide has at least 40 amino acids.

Where the term "part" is used in connection with a nucleotide sequence, the term means a nucleotide sequence comprised by the sequence depicted in SEQ ID No: 1 and having at least 15 nucleotides. More preferably the part has at least 25 nucleotides, and still more preferably the part has at least 40 nucleotides.

The invention also includes a recombinant DNA sequence including a region comprising nucleotides 1413 to 2417 of the sequence depicted in SEQ ID No: 1 or a functional equivalent thereof, or a recombinant sequence comprising a part of said region or said equivalent. Nucleotides 1413 to 2417 correspond to the protein-encoding region of the hsr203J gene which is useful in that the gene product has a functional role in regulating or providing for disease resistance in plants. Thus, the protein coding sequence, or a part thereof, of the hsr203J gene may be fused to an inducible promoter such as that regulating expression of WIN, WUN or PR-proteins so that upon infection by a compatible pathogen, expression of the hsr203J structural gene is induced. The ensuing activation of the hypersensitive response by the hsr203J protein in infected plant cells halts further spread of the pathogen.

The invention also includes a recombinant DNA sequence including a region comprising nucleotides 1 to 1341 of the sequence depicted in SEQ ID No: 1 or a functional equivalent thereof, or a recombinant sequence comprising a part of said region or said equivalent. Nucleotides 1 to 1341 correspond to the non-protein encoding region of the sequence which is 5' to the said protein encoding region. The region of the said DNA sequence comprising nucleotides 1 to 1341 includes the transcriptional regulatory region of the hsr203J gene, including the promoter (binding site for RNA polymerase) and transcriptional silencers and enhancers.

Silencer and enhancer elements are useful in that they enable modulation of the level of expression of the structural genes under their control.

The invention still further includes a recombinant DNA sequence including a region comprising nucleotides 1 to 651 of the sequence depicted in SEQ ID No: 1 or a functional equivalent thereof, or a recombinant sequence comprising a part of said region or said equivalent. The region comprising nucleotides 1 to 651 includes a transcriptional silencer.

The invention still further includes a recombinant DNA sequence including a region comprising nucleotides 652 to 1341 of the sequence depicted in SEQ ID No: 1 or a functional equivalent thereof, or a recombinant sequence comprising a part of said region or said equivalent. The region comprising nucleotides 652 to 1341 includes a transcriptional enhancer and the promoter (ie RNA polymerase binding site) of the hsr203J gene.

The invention further provides the use of hsr203J promoter sequences as affinity substrates for the identification and subsequent purification of hsr203j promoter binding proteins (hsr-PBP's) and proteins associated with these hsr-PBP's. Such hsr-PBP's have been partially characterized, are probably present constitutively and may bind to hsr203J promoter sequences upon incompatible reaction of the host plant such as occurs when *Nicotiana tabacum L.* is inoculated with specific swains of *Pseudomonas solanacearum*.

The invention still further includes a recombinant DNA sequence including a region comprising nucleotides 1195 to 1341 of the sequence depicted in SEQ ID No: 1 or a functional equivalent thereof, or recombinant sequence comprising a part of said region or said equivalent. The region comprising nucleotides 1195 to 1341 includes a bacterial response element which is capable of binding to specific proteins which are produced by pathogens during their infection of tissue, and which are implicated in the development of the hypersensitive response (see above).

The invention still further includes a recombinant DNA sequence including a region comprising nucleotides 1195 to 1268 of the sequence depicted in SEQ ID No: 1 or a functional equivalent thereof, or a recombinant sequence comprising a part of said region or said equivalent. This region more precisely defines the bacterial response element.

The invention still further includes a recombinant DNA sequence as disclosed above wherein the said region, part or equivalent thereof is located on the 5' side of, and is operably linked to, a protein-encoding sequence of a heterologous gene or to a sequence comprising nucleotides 1413 to 2417 of the sequence depicted in SEQ ID No: 1 or a functional equivalent thereof. It is particularly preferred that a translation enhancing sequence is present between the region or part or equivalent thereof, and the protein-encoding region of the DNA sequence 3' thereto.

The heterologous gene may be any suitable structural gene, including a selectable or screenable marker gene or a gene, the product of which is capable of conferring resistance or tolerance to at least one of the following: insects, herbicides, fungi, bacteria and viruses, a marker gene for use in disease pressure forecasting and anti-feedant genes.

The promoter, and/or regulatory regions of the hsr203J gene may be fused to a structural gene encoding a non-diffusible cytotoxie gene product such as an fibonuclease, protease, lipase or glucanase. Induction of expression of such structural genes provides a rapid and localized response to infection by pathogens, and may be useful in providing resistance or improving tolerance of the plant to the pathogen.

Moreover, the regulatory regions of hsr203J gene may be used in the creation of "detector" plants enabling the early detection of disease pressure. The hsr203J promoter and/or regulatory regions thereof, may be fused to a nucleotide sequence providing for a visual alteration to the host plant phenotype upon activation of the promoter by infection. Such sequences include the anti-sense orientation of the gene encoding the Small Subunit of Ribulose B-phospho Carboxylase (SS-RUBISCO) which causes localized bleaching of green tissues. Such sequences could also encode a gene encoding a key enzyme in pigment biosynthesis such as chalcon synthase.

The invention also includes recombinant DNA according to the invention, which is modified in that codons which are preferred by the organism into which the recombinant DNA is to be inserted are used so that expression of the thus modified DNA in the said organism yields substantially similar protein to that obtained by expression of the unmodified recombinant DNA in the organism in which the protein-encoding components of the recombinant DNA are endogenous.

The invention still further includes a DNA sequence which is complementary to one which, under stringent conditions, hybridizes to any one of the above disclosed recombinant DNA sequences.

"Stringent hybridization conditions" are those in which hybridization is effected at between 50° and 60° C. in 2× saline titrate buffer containing 0.1% SDS followed by merely rinsing at the same temperature but in a buffer having a reduced SCC concentration which will not affect the hybridizations that have taken place. Such reduced concentration buffers are respectively (a) 1×SCC, 0.1% SDS; or (b) 0.5×SCC, 0.1% SDS; or (c) 0.1×SCC, 0.1% SDS.

The invention still further includes a DNA vector comprising a recombinant DNA sequence according to the invention or a DNA sequence which is complementary to one which, under stringent conditions, hybridizes thereto.

It is preferred that the vector according to the invention be used to transform a eukaryotic host, preferably of plant origin. It win be appreciated that suitable micro-organisms may be transformed with such a vector, and such micro-organisms represent yet a further embodiment of the invention.

The term "plant" is used herein in a wide sense and refers to differentiated plants as well as undifferentiated plant material such as protoplasts, plants cells, seeds, plantlets etc. that under appropriate conditions can develop into mature plants, the progeny thereof and parts thereof such as cuttings and fruits of such plants.

Preferred vectors will of course vary depending on the chosen host. For dicotyledons, the vector may be introduced into a protoplast by contacting the vector with the protoplast in a suitable medium and under appropriate conditions which render the protoplast competent for the uptake of DNA; the vector may also be employed in the form of an *Agrobacterium tumefaciens* Ti-plasmid derivative which infects plant cells or protoplasts. Monocotyledons are preferably transformed by micro-injection, electroporation or by use of the micro-projectile gun, using the so-called ballistic technique. In any case, appropriate transformation vectors and protocols are well known in the art. The transformed cells or protoplasts are cultured in an appropriate culture medium, and a transformed plant is regenerated in a manner known per se. The introduced nuclear material is stably incorporated into the genome of the regenerated transformed plants which accordingly express the desired genes.

Examples of genetically modified plants according to the present invention include: fruits, including tomatoes, peppers, mangoes, peaches, apples, pears, strawberries, bananas, and melons; field crops such as canola, sunflower, tobacco, sugar beet, small grain cereals such as wheat, barley and flee, corn and cotton, and vegetables such as potato, carrot, lettuce, Brassica oleracea such as cabbage and onion. The particularly preferred plants are sugar beet and corn.

The invention still further includes the progeny or seeds of such plants, and the seeds and progeny of said progeny.

The invention still further includes protein obtained by expression of the recombinant DNA according to the invention, and in particular, expressed protein having the amino acid sequence depicted in SEQ ID No: 2, or a part thereof or a functional equivalent of said sequence or part.

The Invention will be further apparent from the following description, and the associated Figures and Sequence Listings.

Of the Sequences:

SEQ ID No: 1 shows the nucleotide sequence of the hsr203J gene, including the protein encoding region and promoter and transcriptional regulatory elements therefor, isolated from tobacco. The protein coding region of the gene is comprised by nucleotides 1413 to 2417 in the sequence. Putative polyadenylation signals are present 3' to the protein coding region of the gene and the sequence responsible for the HR is within about 1.4 kb of the 5' non-coding region of the gene. In essence the sequence comprises:

a) a 72 bp mRNA leader sequence, located at nucleotides 1341 to 1412 inclusive;

b) CAAT and TATA consensus sequences located at nucleotide positions 1282–1286 and 1313–1316 respectively;

c) the translation start site codon at nucleotide positions 1413–1415;

d) the "deletion promoter" sequence located at nucleotides 1–1341 inclusive which is substantially responsible for the promoter activity;

e) the sequence located at nucleotide positions 1195–1268 having an enhancing effect on the promoter activity;

f) the sequence located at nucleotide positions 1–651 having a silencing effect on the promoter activity.

SEQ ID No: 2 shows the translation product of the hsr203J structural gene, encoded by nucleotides 1413–2417 in SEQ ID No: 1;

SEQ ID No: 3 shows a linker region for a chimeric gene comprising the 5' flanking region of the hsr203J structural gene and the coding region of the uidA reporter gene. The start codon for the hsr203J structural gene is at nucleotides 10–12 in the sequence and nucleotides 13–64 encode the N-terminal sequence of the hsr203J gene product.

EXAMPLES

Bacterial Strains and Plant Material

The source of the *Pseudomonas solanacearum* strains used herein is depicted in Table 1.

TABLE 1

*Pseudomonas solanacearum* wild type and mutant strains used in this study, and their ability to induce symptoms on tobacco

| Strains | Source or reference | Isolated from | Tobacco response |
|---|---|---|---|
| Wild type | | | |
| GMI 1000 | Boucher et al. (1) | Tomato | HR |
| K60 | Lozano et al. (17) | Tomato | Disease |
| Mutants derived from GMI 1000 (deletion of hrp gene cluster) | | | |
| Δhrp | Boucher et al., unpublished | | No symptoms |
| Mutants in hrp gene cluster derived from GMI 1000 (Tn5-B20 mutagenesis) | | | |
| GMI 1462, 1475, 1494, 1492, 1487 | Arlat et al. (18) | | No symptoms |
| GMI 1423, 1425 | Arlat et al. (18) | | Partial and/or delayed HR |
| Mutant derived from GMI 1000 (Tn5-B20 mutagenesis outside the hrp gene cluster) | | | |
| GMI 1485 | Arlat et al. (18) | | HR |

The GMI1000 and K60 isolates are wild-type *P. solanacearum* strains, the former induces the development of an HR on tobacco leaves within 24 h after infiltration, and the latter causes the typical lethal wilting disease. A derivative of the GMI1000 isolate, called Δhrp, deleted for the hrp gene cluster, causes no apparent symptoms in inoculated leaves. Eight mutant strains derived from GMI1000 by transposon Tn5-B20 mutagenesis were used as described below. The GMI1462, 1475, 1494, 1485, 1423 and 1425 strains are each mutated in one of the six putative transcription units of the hrp gene cluster. All these strains have lost the ability to cause an HR on tobacco, except strains GMI1423 and 1425 which are mutated in the right-hand end of the hrp gene cluster, and induce only a partial and/or a delayed HR on tobacco; and the strain GMI1485 which is mutated outside of the hrp gene cluster and elicits a normal HR on tobacco and constitutively expresses the structural gene of β-galactosidase. All these are grown at 28° C. in B or BGT media (1). The cultivars of *Nicotiana tabacum* L. used herein: Bottom Special and Samsun, exhibit similar responses after bacterial inoculation. The seedlings are grown in vitro on Murashige and Skoog (MS) medium (2) during 4 to 5 weeks (25° C., 16 h photoperiod, 15 Watt/m$^2$), and then transferred to soil in a growth chamber (25° C., 16 h photoperiod, 30 Watt/m$^2$).

Isolation of hsr203J gene, and nucleotide sequence analysis

A tobacco (*Nicotiana tabacum* L. cultivar NK326) genomic library constructed in the bacteriophage λ-Embl3 (Clontech) is screened with the pNt203 cDNA clone (3). The PstI insert of pNt203 is labeled by the random primer technique (4). Replicate nitro-cellulose filters of the genomic library are treated and hybridized as suggested by the manufacturers (Amersham). Four different genomic clones including hsr203J are isolated. Exonuclease III deletions are performed at both ends of DNA inserts subcloned in the phagemid pKS (Stratagene) according to Henikoff (5), and both strands are sequenced by the dideoxy chain termination method (6) using Sequenase (US Biochemical, Corp.). Sequence compilation and analysis are performed by using the Genetics Computer Group software of the University of Wisconsin (7). Homology searches with the Genebank (release 71.0) and Swissprot (release 21.0) data bases are performed using the FASTA algorithm (8). The protein sequences are analysed for potential N-terminal signal sequences and membrane-spanning domains using release 5.0 of the PC/Gene Programme (Department of Medical Biochemistry, University of Geneva, Switzerland). The transcription start site is determined by the primer extension technique using polyA+ RNA extracted from tobacco leaves 9 hours after inoculation with the incompatible isolate and an oligonucleotide located at the ATG codon (nucleotides 1413 to 1415 in SEQ ID No: 1).

Reporter gene constructs

A 2.2 kilobase (kb) BglII fragment containing 1.3 kb of the 5' non-coding region of the tobacco hsr203J gene and 890 base pairs (bp) of the nucleotide sequence downstream of the transcription start site is cloned into the BamHI site of phagemid pKS, to produce pKJ2.2. This plasmid is digested with BstBI, which cuts once 55 bp 3' of the hsr203J translation initiation codon, and the BstBI generated ends were blunt end ligated by the Klenow fragment of DNA polymerase before digestion with SalI. This 1.5 kb SalI—BstBI fragment is cloned into the SalI—SmaI site of the β-glucuronidase (GUS) expression binary vector pBI101.2 (9) to produce the hsr203J- uidA gene fusion pHG21A. A 3.5 kb HindIII—EcoRI DNA fragment of pHG21A, including the hsr203J promoter and the uidA coding sequence, is ligated into the HindIII—EcoRI digested pUC19 vector to produce pHG21, for transient expression gene assays (FIG. 1). The pHG21 and pHG21A constructs therefore contain 1341 bp 5' non coding sequence, the 72 bp leader sequence, the first 55 bp of the coding sequence of hsr203J fused in frame with the GUS coding sequence, and the nopaline synthase (nos) gene polyadenylation signal. The translational fusion is confirmed by direct double-stranded sequencing with a GUS specific primer (10). Two additional plasmids, pBI201 and pBI221, contain respectively a promoterless uidA gene, and a cauliflower mosaic virus (CaMV) 35S promoter—uidA gene, upstream of the nos terminator, in the pUC19 vector (Clontech).

Protoplast isolation and transient expression assays

Leaves of 4 to 5-week-old in vitro grown tobacco plants, cultivar Samsun NN, are used for isolation of protoplasts by incubating leaf sections in TO medium (11) containing 1 g/L cellulase R 10 Onozuka, 200 mg/L macerozyme Onozuka (Yakult Honsha, Nishinomiya, Japan) and 500 mg/L pectolyase Y23 (Seishin Pharmaceutical Ind.), for 15 h at 22° C. in darkness. Protoplasts are separated from the cellular debris by sieving through an 85 μm nylon mesh followed by centrifugation at 50 g for 5 min onto a 1 mL cushion of 19% (w/v) sucrose. Floated protoplasts are washed once with TO medium, counted, and adjusted to the density of $1.5 \times 10^6$ protoplasts/mL. Transformation is performed by incubating the protoplasts (320 μL samples) at 45° C. for 5 min, after a brief cooling at room temperature, by adding plasmid DNA (50 μg per assay in 10 mM Tris-HCl, pH 8) and 160 μL of a PEG solution (40% PEG, 0.4 M mannitol, 30 mM $MgCl_2$, 0.1% Mes pH 5.8). Protoplasts are gently mixed for 10 min at room temperature. They are then collected by centrifugation and resuspended in 500 μL TO medium. The bacterial suspension (10 bacteria/protoplast) prepared as previously described (12) is then added. After incubation at 28° C. for 24 h, the protoplasts are lysed by the addition of 50 μL of 10X GUS buffer, centrifuged and the supernatant is assayed for GUS activity (10).

Transgenic tobacco plants pHG2A, pBI121, and pBI101 are mobilised from *Escherichia coli* DH5α into *Agrobacterium tumefaciens* strain LBA 4404 (13) and transgenic tobacco plants (*N. tabacum*, Bottom Special) are generated by the leaf disk method (14). Transformed plants are selected on MS medium containing 0.8% Difco agar, kanamycin at 100 μg/mL and carbenicillin at 500 μg/mL. Transgenic plants are self-fertilized and seeds are collected. Their genotypes are determined by progeny (T2) analysis, by germination on MS medium containing kanamycin (500 μg/mL).

Inoculation of transgenic plants with bacterial isolates

All the inoculation experiments are performed on kanmycin-resistant T2 plants, with at least 2 plants of the same genotype per experimental condition. For the screening of transformants and kinetic experiments, tobacco leaves are detached from 8 week-old plants and infiltrated in vacuo with the bacterial suspension ($10^7$ c.f.u./mL) or water as described in ref (12). Syringe infiltration experiments are performed on 8 week-old plants by infiltrating the bacterial suspension ($10^8$ c.f.u./mL) into a small region of unclelathed leaves with a syringe without a needle. For some experiments, inoculations were performed on 5 week-old plants grown in Magenta cubes (Sigma) on MS medium. Each half of a leaf is perforated 6 times with an 10 μL-Hamilton needle and a 3 μL droplet of bacterial suspension ($10^8$ c.f.u./mL in 0.4% Difco agar) is immediately deposited at the wounded sites.

For localized root inoculation, 4 week-old plants are grown on a raft (Sigma) in contact with MS medium containing 0.2% Difco agar, and inoculated with a 3 μL droplet of bacterial suspension through a wound made with a needle at one centimeter from the root apex or at a secondary root emergence. For generalized root inoculation, the whole plant is detached carefully from the raft, avoiding wounding, and the root system is immersed in 7 mL of the bacterial suspension ($10^8$ c.f.u./mL).

Inoculated plants are maintained at 28° C., and analysed either directly or stored at −80° C. after incubation time.

GUS assays

Plant tissue is ground in liquid nitrogen, homogenized in 1X GUS buffer, centrifuged for 5 min at 10,000 g and the supernatant assayed for GUS activity, as previously described (15). Protein concentration is determined using the Bradford dye reagent GUS activity is expressed as picomoles of 4-methylumbelliferone per min per mg of protein. Alternatively, histochemical assays are performed on fresh tissue using X-glue (5-bromo-4-chloro-3-indolyl-β-D-glucuronide, Clontech) or Magenta-gluc (Biosynth AG) as the substrate (10). For some experiments, samples are fixed in 0.3% formaldehyde/50 mM $NaPO_4$ buffer pH7, then cleared by boiling in ethanol and stored in ethanol 70%.

β-galactosidase assays

Following the GUS histochemical assay, some samples are equilibrated in Z' buffer (16) (100 mM $NaPO_4$ buffer pH 7.4, 10 mM KCl, 1 mM $MgSO_4$), fixed in 1.25% glutaraldehyde for 1 h in order to inactivate endogenous plant β-galactosidases, rinsed and stained at 28° C. with 0.8 mg/mL Magenta-Gal (Biosynth Ag) or X-gal in Z' buffer containing 5 mM $K_3FeCN)_6$ and 5 mM $K_4Fe(CN)_6$, then cleared by boiling in ethanol and observed by dark- or bright-field microscopy.

Characterization of hsr203J gene

The hsr203J gene is isolated by screening a genomic tobacco library with pNt203 cDNA clone. It belongs to a small multi-gene family consisting of a minimum of 4 genes (see ref. 3) and at least 2 genes of this family corresponding to 2 different cDNA clones (pNt203 and pN1239) are expressed during the HR.

Sequence analysis of the 2.7 kb DNA region of hsr203J (SEQ ID No: 1) reveals a single open reading frame (ORF) with no intron and a potential coding capacity of 355 amino acids. The nucleotide sequence of the said 2.7 kb region is identical to the pNt239 cDNA clone except for 2 substituted bp (not shown). These mismatches are probably due to the isolation of the genomic and cDNA clones from different tobacco cultivars: the genomic clone is isolated from cultivar NK326 whereas the pNt239 cDNA clone is obtained from the cultivar Bottom Special. The predicted hsr203J structural protein (SEQ ID No: 2) has a Mr. of 37.5 kDa and a theoretical isoelectric point of 5.17.

The transcription start site is mapped by primer extension to a position 72 bp upstream of the putative translation initiation codon. The promoter and 5'-untranslated region exhibited no obvious sequence homology to cis-elements already described in defense genes.

Figure 2:
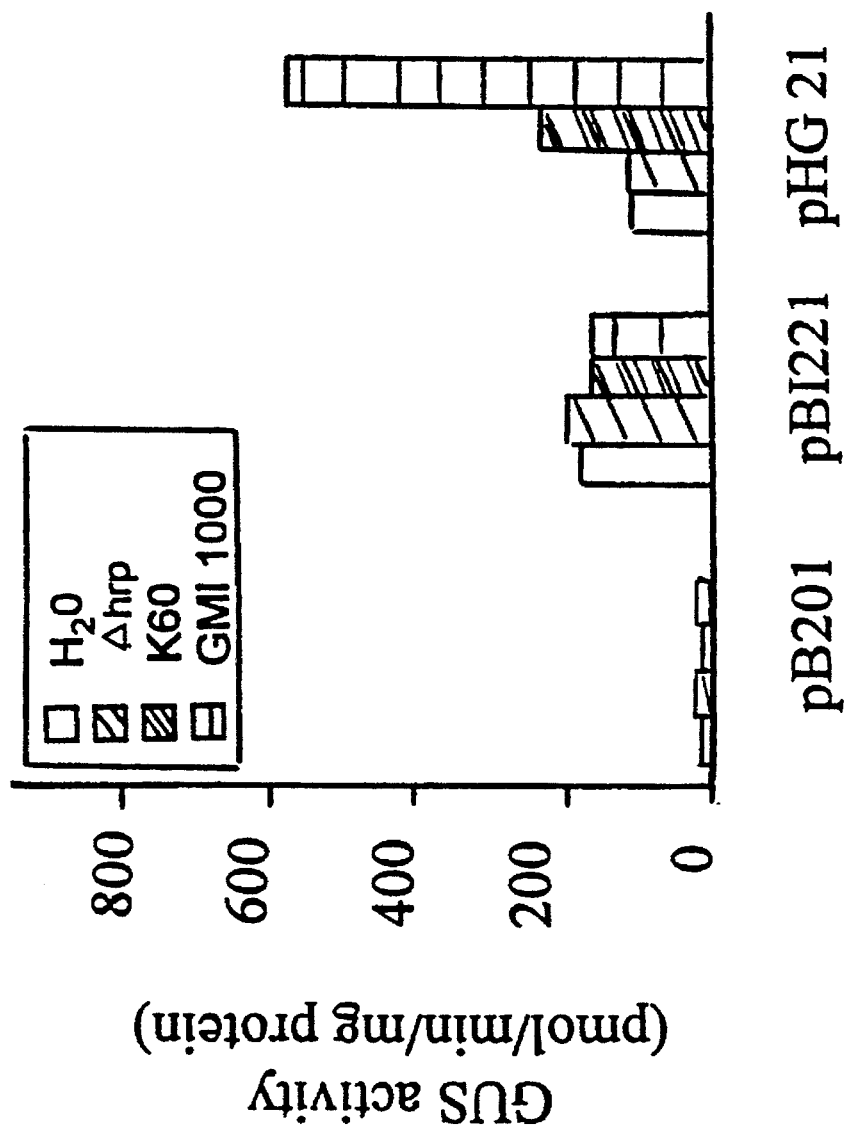
FIG. 2 shows the effect of infection with different isolates (hrp, K 60 and GMI 1000) of *Pseudomonas solanacearum* on hsr203J promoter activity in transformed tobacco protoplasts. As a control, water was added to the protoplasts. Plasmid pBI201 and pBI221 are respectively negative and positive control plasmids; pHG21 is the hsr203J-uidA gene fusion. GUS activity assays were preformed 24 h after incubation. The data shown represent the mean of three separate experiments.

Transient expression of the hsr203J-uid A gene fusion in tobacco protoplasts pHG21 plasmid is composed of a translation fusion between 1.4 kb of the 5' flanking sequence from the hsr203J gene and the coding region of the uidA reporter gene, linked to the 3' untranslated region of the nopaline synthase gene (FIG. 2). The plasmids pBI201 and pBI221 are used respectively as negative and positive controls in transient assays.

Figure 3:
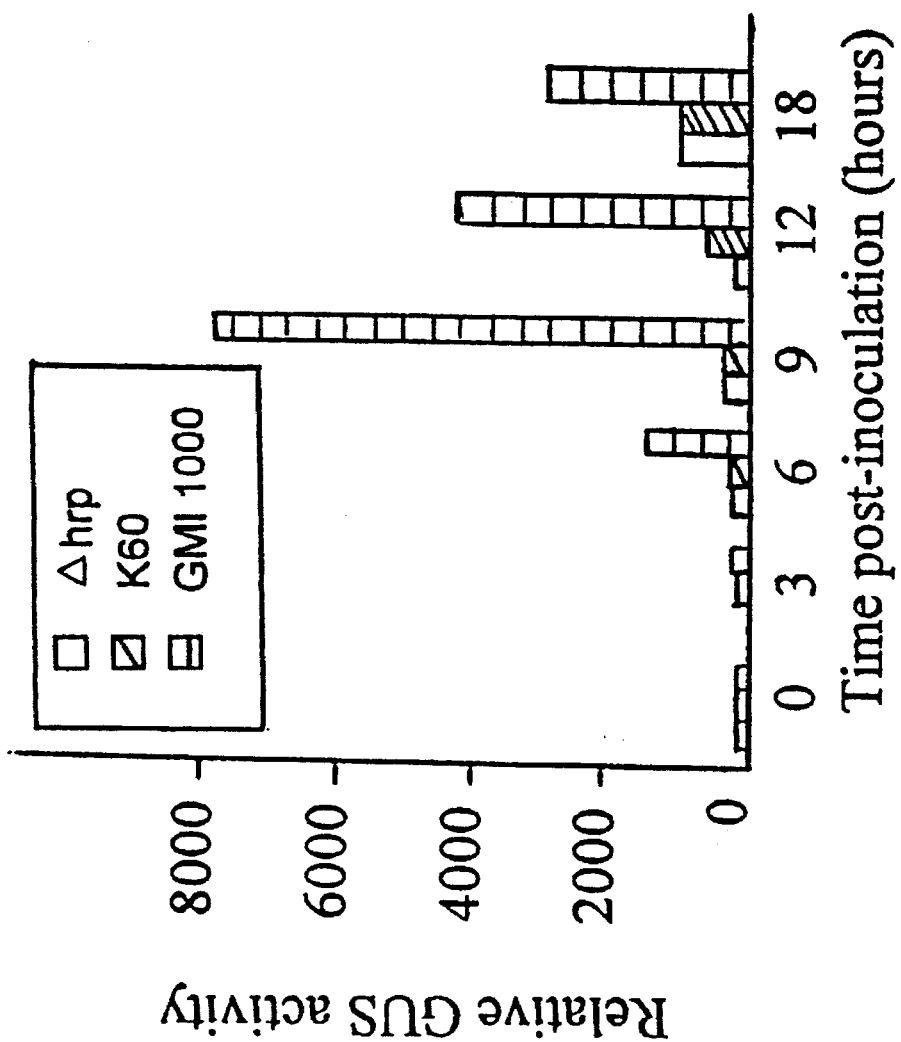
FIG. 3. Shows the time course of hsr203J promoter activation of the GUS gene in transgenic tobacco leaves infiltrated with different isolates (hrp, K 60, and GMI 1000) of *Pseudomonas solanacearum*. GUS activity was measures in extracts of four leaves from two pHG21-14A transformants.

Initial experiments show that protoplast viability as quantified by Evans blue exclusion is not significantly altered in the presence of bacteria at 10 to 100 bacteria per protoplast (data not shown). Subsequenfiy experiments are performed with 10 bacteria per protoplast. At this bacterial density, the expression of GUS fused to the hsr203J promoter in response to GMI1000 isolate is 6-fold higher than in response to the controls (water or Δhrp inoculation) (FIG. 3). In comparison, inoculation with the compatible isolate, K60, led to a 2-fold increase in enzyme activity. These levels of GUS activity have to be compared with those measured in protoplasts transformed with the CaMV 35S-uidA gene fusion (pBI221) which exhibit a high and almost constitutive level after the various inoculation treatments (FIG. 3).

The results of transient assays therefore indicate clearly that the hsr203J promoter contains all the necessary elements for its preferential activation by the HR-inducing bacterial isolate, and that this expression system perfectly mimics the plant/pathogen interaction.

Expression of hsr203J-uid A gene fusion in transgenic tobacco

In order to determine the spatial and temporal patterns of expression of the hsr203J promoter in planta, the hsr203J-uidA gene fusion is transferred to tobacco by leaf disk transformation. T2 plants resistant to kanamycin are used in all the experiments. Of 23 kanamycin resistant transformants, 20 expressed the gene fusion and these all exhibit the same overall pattern of expression: GUS activity is found maximal after infiltration with GMI1000, with a 2- to 90-fold stimulation over control infiltrations (water or Δhrp), and a 2- to 25-fold induction over K60 infiltration, 18 hours after inoculation (not shown). These levels are comparable to those obtained in transient experiments after inoculation by GMI 1000 or K60.

Based on this analysis, a transformant (pHG21-14A) which displays a 90-fold stimulation of GUS activity after incompatible inoculation compared to control infiltrations, and contains one insertion of the gene fusion per haploid genome, is selected. The presence of a native gene fusion is checked by Southern analysis of genomic DNA (not shown).

Assay of extractable GUS activity and GUS histochemical localization are both used to monitor the activity of the hsr203J promoter in different organs during plant development and in response to bacterial inoculation. No GUS activity was detected in 4, 7 or 15 day-old pHG21-14A tobacco seedlings, either in healthy leaves, or in flowers of fully grown plants (data not shown). These data indicate that the hsr203J promoter is strongly activated in leaves inoculated with the HR-inducing isolate, GMI1000, 18 h after infiltration, as indicated by the screening of all the transformants obtained. A kinetic study is performed on transformant pHG21-14A (FIG. 3), which shows that in leaves infiltrated with GMI1000, GUS activity increases to a level 12-fold over control values 6 h after inoculation, reaches a maximum of 200-fold stimulation at 9 h, and decreases to an intermediate level (80-fold induction) upon longer incubations. Much lower levels are measured after K60 infiltration, and undetectable levels of GUS activity were found in leaves infiltrated with water or the Δhrp isolate at any incubation time.

Plants transformed with the promoterless construct pHI101 show negligible levels of GUS activity. Moreover, plants transformed with pBI121, which contain a CaMV 35S-uid A gene fusion, show similar levels of enzyme activity, whatever the nature of the inoculum (not shown). Thus the hsr203J-uid A gene fusion exhibits a distinct and specific pattern of activation upon bacterial inoculation of transgenic tobacco plants that closely matches the in vivo pattern of accumulation of hsr203J transcripts in infiltrated tobacco leaves (3). These results also indicate that hsr203J promoter is early and specifically activated during an incompatible plant/pathogen interaction, and that its induction is hrp gene-dependent since the bacterial isolate which is deleted of hrp genes is unable to activate the hsr203J promoter.

Localization of hsr203J-uidA activation in response to bacterial inoculation

Different inoculation tests are performed on transformants pHG21-14A in order to localize precisely hsr203J promoter activation in response to bacterial inoculation; first, in tobacco leaves in order to investigate promoter induction during a typical HR, and secondly, in roots, which are the organs naturally infected by the bacteria.

Figure 4A:
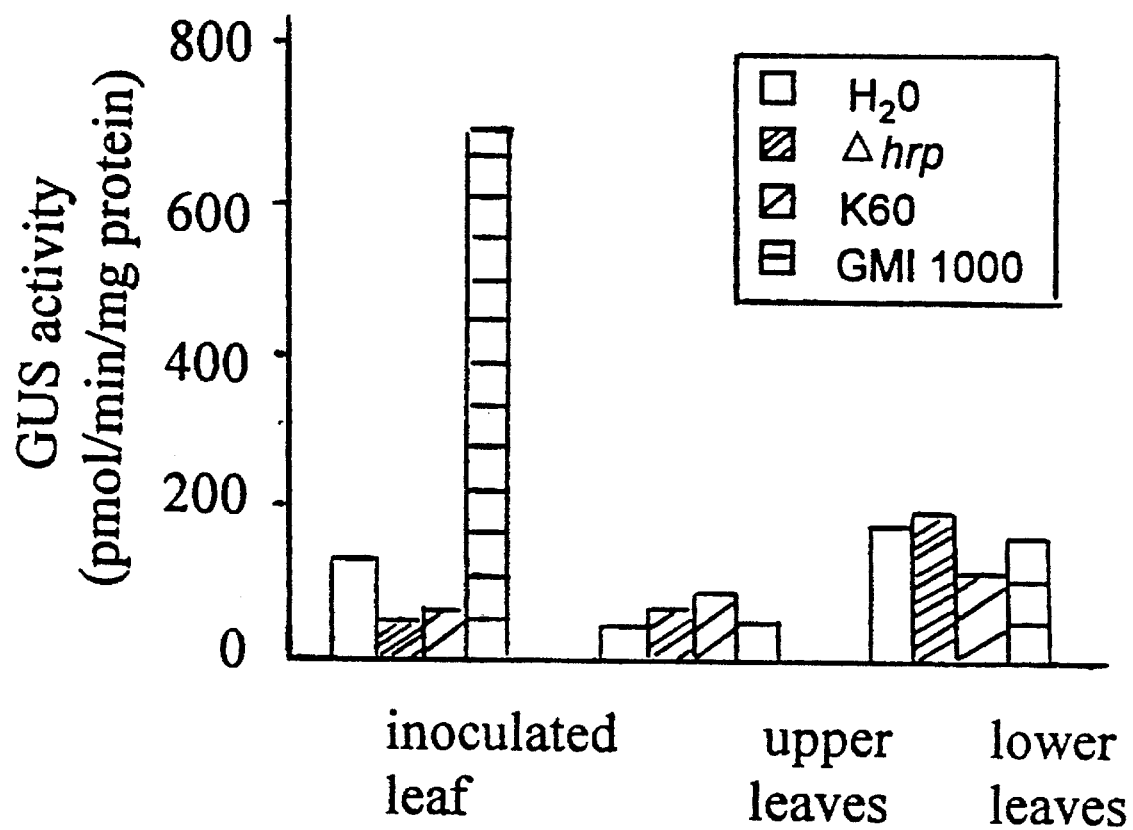
FIG. 4(A) shows the induction of β-glucuronidase (GUS) activity in the bacterial-inoculated third leaf, and in the upper and lower un-inoculated leaves of transgenic tobacco.
Figure 4B:
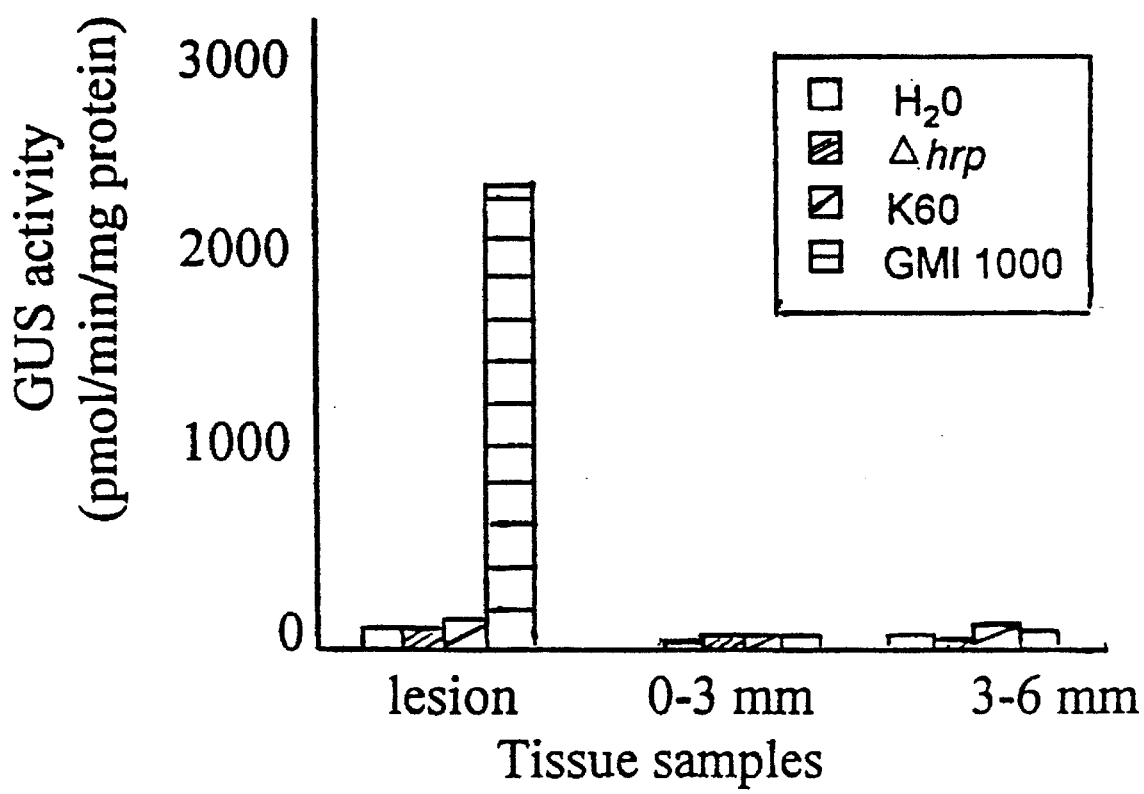
FIG. 4(B) shows the induction of β-glucuronidase activity in and around the lesion of the inoculated third leaf. The following tissue samples were assayed: lesion meaning necrotic tissue resulting from the wounding and/or bacterial infection; 0—3 mm meaning apparently healthy tissue up to 3 mm from the lesion; 3–6 mm meaning apparently healthy tissue 3 to 6 mm surrounding the lesion. Inoculation was performed on pHG21-14A transformants. Small leaf perforations were covered by a droplet of the bacterial suspension (3 μL containing $10^8$ c.f.u./mL) or water, as indicated on the Figure. Tissue samples were collected 18 h after inoculation.

Leaf inoculations:

In order to test whether the hsr203J-GUS gene expression is local or systemic, leaves of 5 week-old transgenic plants are inoculated with bacterial suspension droplets. After incubation for 18 and 70 hours, GUS activity is determined in haft of the inoculated leaf as well as in upper and lower leaves. The results show a 15-fold induction of this activity in the inoculated leaf, whereas very low levels are detected in the lower and upper leaves (FIG. 4A). The other half of the inoculated leaf is used for histochemical GUS assay. A narrow blue-stained region is visualized 18 h and 70 h after inoculation with the HR-inducing bacterial isolate, surrounding the wounded area, which is restricted to a few cell layers and is localized very close to yellowing, probably dead, cells. The intensity of the staining increases 70 h after inoculation. Only a few dispersed cells exhibit a faint blue staining after K60 inoculation; water or Δhrp isolate inoculations induce no detectable GUS expression. Staining of transgenic plants harboring a chimeric uidA gene under the control of the CaMV 35S promoter results in the staining of the entire leaf, with no preferential staining around the lesions, thus demonstrating the specific nature of the induction of the hsr203J promoter in this area. A more detailed localization of this activation during infection is provided by GUS activity measurements in small squares surrounding the lesion, 18 h after inoculation (FIG. 4B). High levels of enzyme activity (48-fold stimulation over control values) are found only within the necrotic lesion itself after inoculation by GMI1000. No detectable enzyme activity is found in tissue up to 3 mm away from the lesion.

In order to determine how early the hsr203J promoter is activated in the inoculated area, histochemical GUS localizations are performed on leaves of 8 week-old transgenic plants locally infiltrated by a syringe with the bacterial suspensions or K60. As early as 6 h after inoculation by the GMI1000 isolate at which time there is no visible tissue necrosis, the leaf infiltrated area shows a blue staining whose intensity increases 9 h after inoculation. At later incubation time points, a yellow necrosis progressively appears, limited on its border by a thin blue area still located within the infiltrated part of the leaf.

These different experiments show clearly that hsr203J-GUS expression is confined to a restricted area corresponding precisely to cell layers infected by the HR-inducing isolate, GMI1000.

Root inoculations:

Roots of transgenic plants gown on rafts are wounded and inoculated with a droplet of bacterial suspension. After 48 h incubation, histochemical localization of GUS activity is performed. Staining only observed in roots infected by GMI1000 extends from the initially inoculated site to a 2 mm distance in the root. Cytological studies indicate that hsr203J promoter activation appears not to be cell-type dependent (not shown). A generalized root inoculation is also performed by simply immersing the whole root system in a bacterial suspension. In this case, GUS activity is found in restricted regions of the roots, i.e. at the point of origin of secondary roots. Expression of the gene fusion at this specific location has to be correlated with the existence of preferential sites of bacterial entry into the host which have been observed along the emergence sheath of secondary roots. At these specific sites, a double staining of GUS activity and bacteria by using a bacterial isolate containing a β-galactosidase fusion, shows a good correlation between the activation of the hsr203J promoter and the presence of bacteria. A superficial and intercellular bacterial colonization of the root tips has also been observed and results in a strong activation of the hsr203 promoter in this part of the root.

Thus, the hsr203J-GUS gene fusion exhibits a distinct and specific pattern of activation in transgenic tobacco plants in response to bacterial infection and one which closely matches the pattern of bacterial ingress into the plant.

Dependence of hsr203J-uidA activation on hrp genes

Figure 5A:
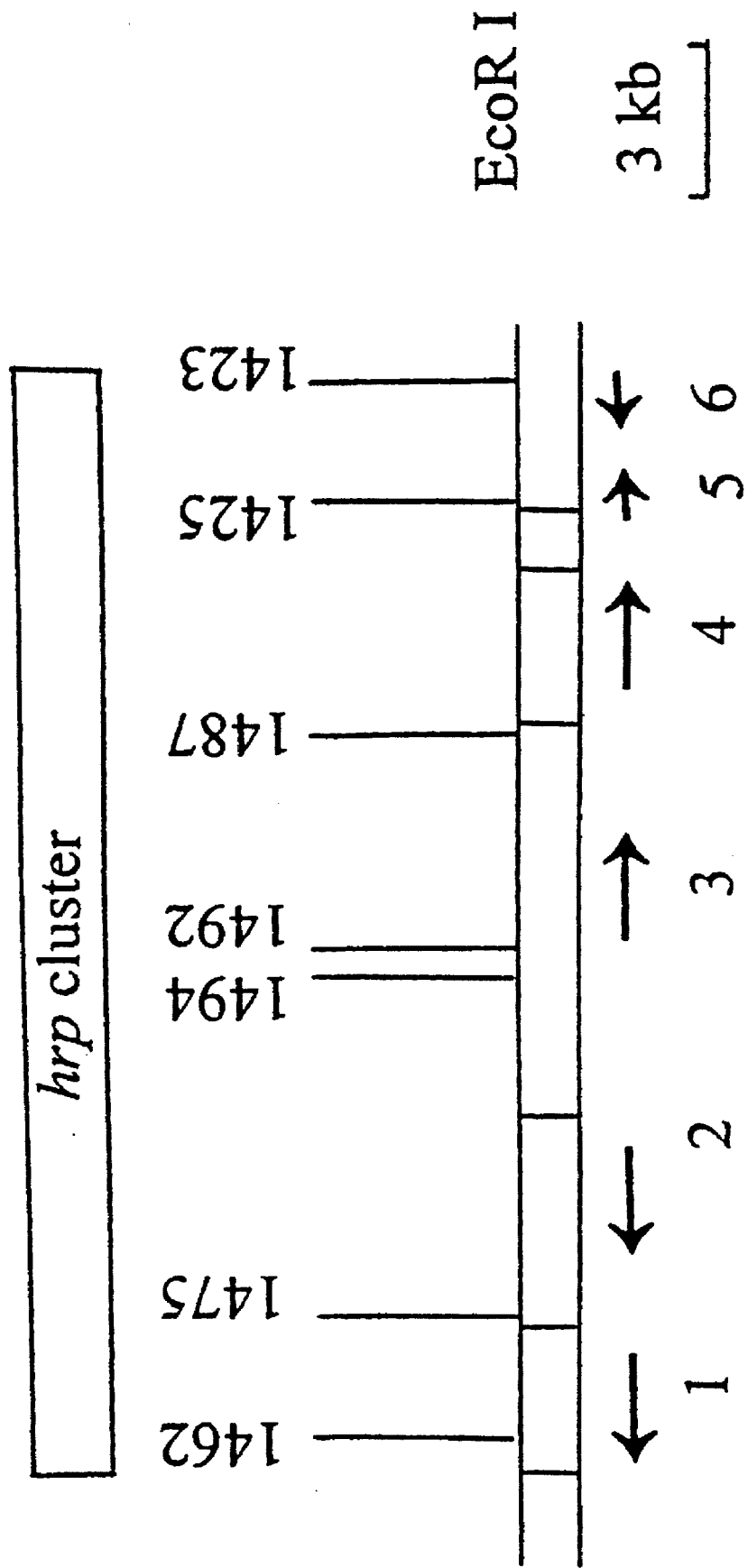
FIG. 5(A) shows the effect of hrp mutants on the activation of hsr203J promoter in transgenic pHG21(14A) tobacco plants. Specifically depicted is the localization of hrp mutations in the different transcription units of the hrp gene cluster.
Figure 5B:
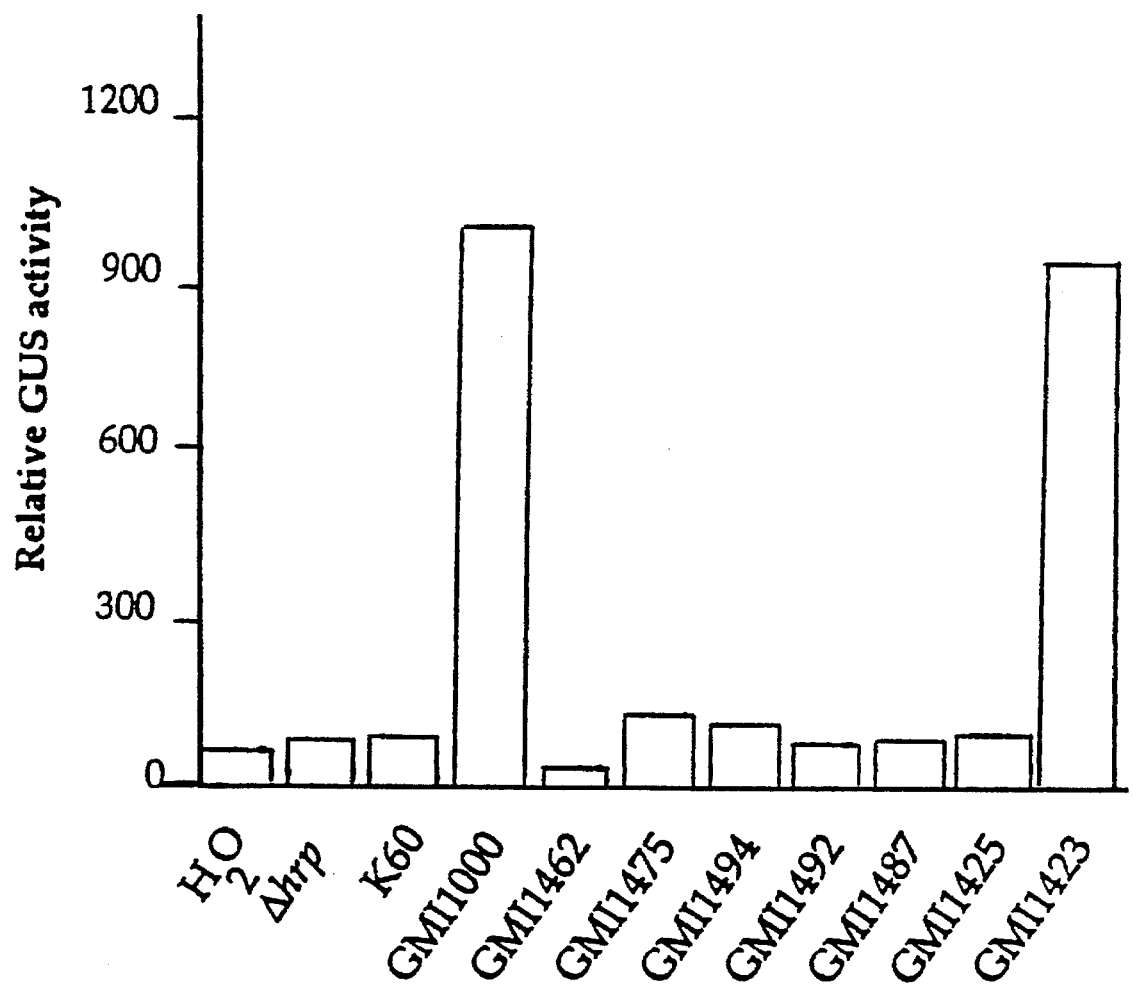
FIG. 5(B) shows measurement of GUS activity in leaves at 18 h after inoculation by the hrp K60 or GMI 1000 isolates or by water, or by the hrp mutants indicated in FIG. 5(A). Inoculation was performed as described in FIG. 4(A) and (B).

Different *P. solanacearum* strains mutated in one of the six transcription units of the hrp gene cluster (FIG. 5A) are used to inoculate transgenic plants (pHG21-14A) by the droplet method. These mutant strains have lost the ability to induce an HR on tobacco, although two of them, GMI1425 and GMI1423, lead to a partial or delayed HR. 18 h after incubation, no effect on GUS activity can be detected with 6 out of 7 tested mutants; only GMI1423 leads to an increase in enzyme activity comparable to that of the wild type strain, GMI1000 (FIG. 5B). These data indicate that hsr203J activation requires almost a whole functional hrp gene cluster.

Until now, no plant gene has been identified which is specifically implicated in the perception of an incompatible pathogen, the transfer of that signal throughout the cell or finally the programmed cell death (HR) which provides an efficient mechanism for the limitation and eventual elimination of the pathogen.

The gene hsr203J (SEQ ID No: 1) is the first hypersensitivity-related gene to be isolated, whose promoter exhibits a rapid, high-level localized and specific activation in response to an HR-inducing bacterial isolate.

Construction of deletions of the 5' promoter region of pHG21

Figure 6:
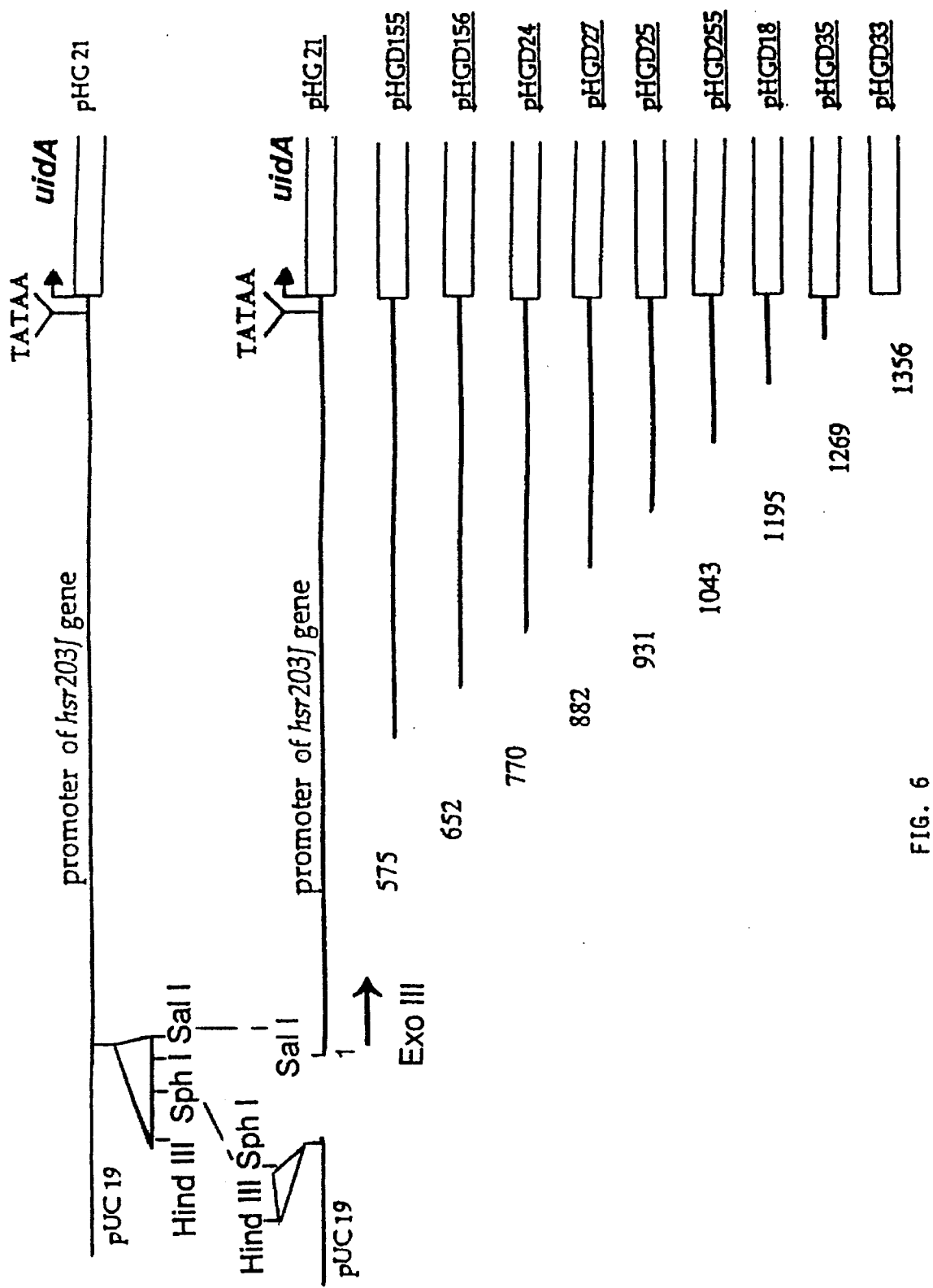
FIG. 6 shows schematically the construction of plasmids pHGD having serval deletions of pHG21.

Unidirectional deletions of the promoter of the chimeric gene have been realized starting from the 5' end according to Henikoff (5). For that purpose, plasmid pHG21 (FIG. 1) is linearised employing the restriction enzymes ShpI and SalI, and then digested by exonuclease III. Constructions having successive deletions, each distant by ca. 200 pb, are selected. The localization of the 5' end of the deletion is determined by sequencing the region and comparison with the nucleotide sequence of the hsr203J gene (see FIG. 6).

Effect of deletions on gene expression of the chimeric gene in transgenic tobacco plants 50 μg plasmid DNA corresponding to the different deletions (FIG. 6) are introduced by transformation into tobacco plants. The GUS activity is measured 18 hours after inoculation.

Figure 7:
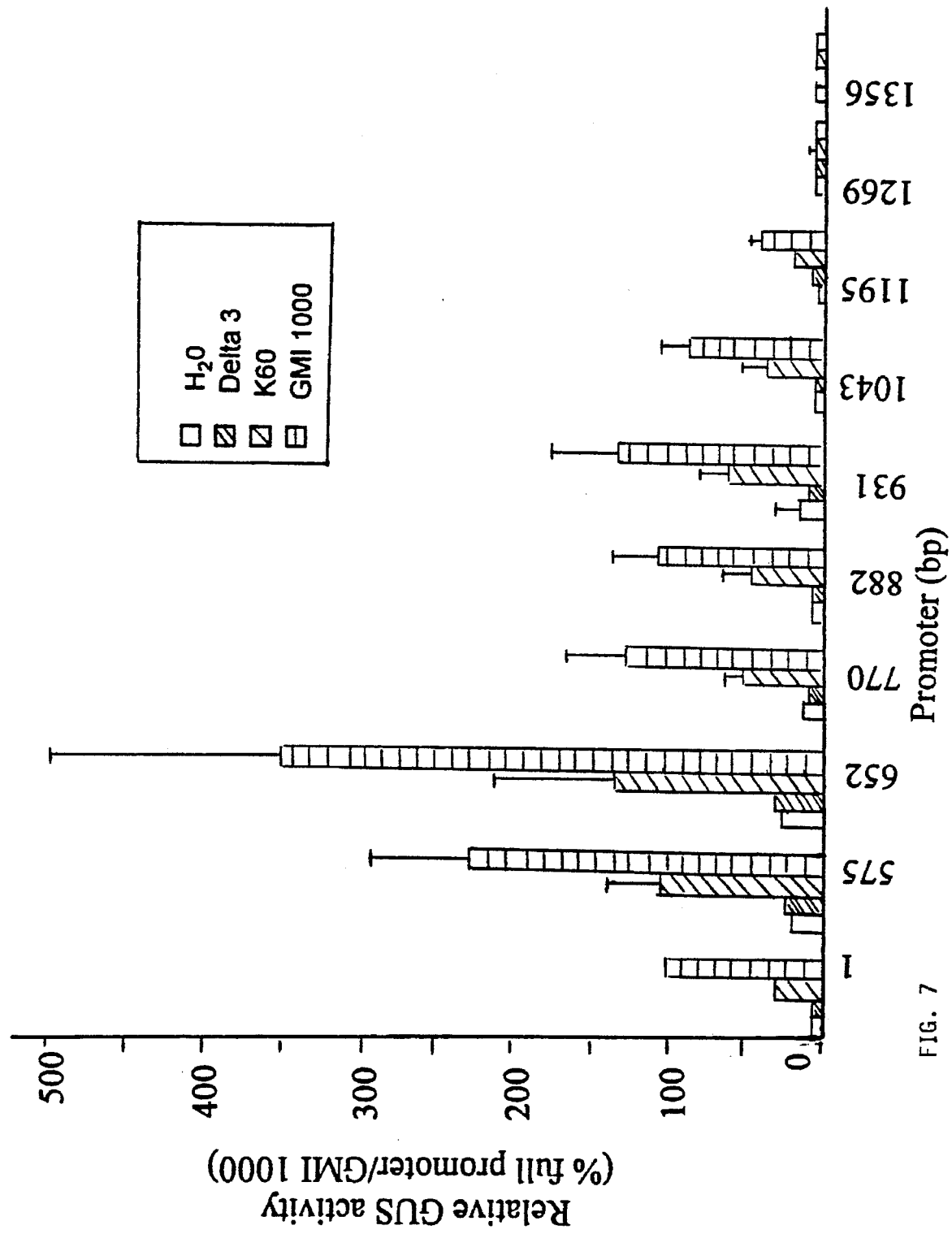
FIG. 7 shows in transgenic tobacco plants the expression of the GUS gene by constructs obtained by 5' promoter deletions of pHG21 (According to the scheme of FIG. 5(A) and 5(B)). The plants were transformed with 5μg DNA, and the value 100 was given to the GUS activity obtained by transformation with the pHG21 construct. The Figure shows the increase in activity (After 18 hours) of the GUS gene as a consequence of infiltration of the transformed plants with the bacterial strains Delta 3, K60 and GMI 1000. As controls plants were infiltrated with water.

FIG. 7 shows the expression of the GUS gene by constructs obtained by 5' promoter deletions of pHG21 (according to the scheme of FIG. 5). The plants were transformed with 5 μg DNA, and the value 100 was given to the GUS activity obtained by transformation with the pHG21 construct. The Figure shows the increase in activity (after 18 hours) of the GUS gene as a consequence of infiltration of the transformed plants with the bacterial strains Delta 3, K60 and GMI 1000. As controls plants were infiltrated with water. These experiments indicate the presence of 2 main regions having a regulatory effect of the deletion promoter of the hsr203J gene.

One or more elements situated in the 1–651 nucleotide region of SEQ ID No: 1 are responsible for a diminution of the expression of the chimeric gene, and elements situated in the second region (nucleotides 652–1268) exhibit a positive effect on the activation of the promoter of the hsr203J gene.

The study of the spatial and temporal patterns of promoter activation in roots and leaves of transgenic plants inoculated with *Pseudomonas solanacearum*, indicate that the promoter is specifically activated during the HR several hours before the appearance of the necrotic lesion the localization of its activation is restricted to the few cell layers in contact with the bacteria the promoter does not respond to various stress conditions and is very weakly activated during compatible interactions the promoter activation is strongly dependent on hrp (hypersensitive response and pathogenicity) genes of *Pseudomonas solanacearum*. These genes control the ability of the bacterium to elicit the HR in resistant or non-host plant and to cause the disease on the host plant.

In favour of a major role of the bacterial hrp genes in the activation of hsr 203J gene promoter, is the fact that the hsr 203 promoter is expressed in response to an HR specific elicitor, harpin, product of one of the hrp genes of *Erwinia amylovora*. In response to this polypeptide, the promoter is activated at similar levels to those observed with the corresponding avirulent strain, but more rapidly. Other potential inducers such as biotic and abiotic elicitors, resistance inducers, do not affect its expression. The generality of the specific expression of hsr 203J during incompatible interactions with bacterial pathogens has been demonstrated by testing other pathogens such as *Pseudomonas syringae* pv pisi/*pseudomonas syringae* pv tabaci, and *Erwinia amylovora*.

In addition the functional analysis of the cis elements responsible for the transcriptional activation of the hsr 203J gene in response to the incompatible bacterial strain, has been initiated by generating a series of 5' deletions and analysis of these constructs by transient assay and in transgenic plants. The results reveal the presence of a distal silencer element, and of two positive regulatory elements, one being quantitative (nucleotides 655–770 in SEQ ID No: 1), the other one being specific for the response to the bacterium, between nucleotides 1195 and 1268 of the SEQ depicted in SEQ ID No: 1.

These results indicate that the hsr 203J gene promoter exhibits new and original characteristics of activation with regard to plant defense genes studied so far; its spatial and temporal program of activation together with its specific induction during the HR underline the importance of this gene as a molecular tool to study the establishment and regulation of the HR. In addition, a 74 bp sequence element has been defined as responsible for the inducibility of the promoter by the avirulent pathogen.

Although the invention has been specifically described with reference to activation of the hsr203J promoter in response to challenge of Tobacco plants with an incompatible pathogen, it will be appreciated that the promoter may likewise be activated by challenge of other plants transgenic for the gene with other pathogens, including certain viruses and certain fungi, indicating that specific expression of the hsr203J promoter is a general phenomenon of incompatible interactions between host and pathogen which lead to the hypersensitive response.

Moreover, the nucleotide sequence comprised by positions 1195 to 1268 of the sequence depicted in SEQ ID No: 1 containing the bacterial response element binds to nuclear protein extracts from various sources (healthy plants, plants inoculated with *Pseuclomonas solanacearum* strains: compatible, incompatible and the hrp- mutant, after different incubation times). Such binding may be estimated by retardation gel analysis using, for example, the 74 bp region and several sub-fragments thus enabling identification of discrete sequences within the BRE region which are useful in providing genetic constructs comprising inducible disease resistance genes.

REFERENCES

1. Boucher, C. A., Barberis, P. A., Trigalet, A. P., & Demery, D. A. (1985) J. Gen. Microbiol. 131, 2449–2457.
2. Murashige, T. & Skoog, F. (19629 Physiol. Plant 15, 473–497.
3. Marco, Y. J., Ragueh, F., Godiard, L., & Froissard, D. (1990) Plant Mol. Biol. 15, 145–154.
4. Feinberg, A. P. & Vogelstein, B. (1983) Anal. Biochem. 132, 6–13.
5. Henikoff, S. (1984) Gene 28; 351–359.
6. Sanger, F., Nicklen, S. & Coulson, R. (1977) PNAS. (USA) 74, 5463–5467.
7. Devereux, J., Haeberli, P. & Smithies, O. (1984) Nucleic Acids Res. 13, 387–395.
8. Pearson, W. R., and Lipman, D. J. (1988) PNAS. (USA) 85, 2444–2448.
9. Jefferson, R. A., Kavanagh, T. A. & Bevan, M. W. (1987) EMBO J. 6, 3901–3907.
10. Jefferson, R. A. (1987) Plant Mol. Biol. Reporter 5, 387–405.
11. Chupeau, Y., Bourgin, J. P., Missonier, C., Dorion, N. & Morel, G. (1974) Compte-rendu à l' Académie des Sciences Paris 278, 1565–1568.
12. Ragueh, F., Lescure, N., Roby, D. & Marco, Y. (1989) Physiol. Mol. Plant Pathol. 35, 23–33.
13. Bevan, M. W., (1984) Nucleic Acids Res. 12, 8711–8721.
14. Horsch, R. B., Fraley, R. T., Rogers, S. G., Sanders, P. R., Lloyd, A. & Hoffmann, N. L. (1984) Science 223, 496–498.
15. Roby, D., Broglie, K., Cressman, R., Biddle, Pl, Chet, I., & Broglie, R. (1990) Plant Cell 2, 999–1007.
16. Teeri, T. H., Lehvaslaiho, H., Franck, M., Uotila, J., Heino, P., Palva, E.T., Van Montagu, M. and Herrera-Estralla, L. (1989) EMBO J. 8, 343–350.
17. Lozano, J. C. & Sequeira, L. (1970) Phytopathol. 60, 833–838.
18. Arlat, M., Gough, C. L., Zischek, C., Barberis, P. A., Trigalet, A., & Boucher, C. A. (1992) Mol. Plant Microbe Interact. 5, 187–193

We claim:

1. Purified protein obtained by the expression of recombinant DNA wherein said DNA comprises the nucleotides 1413 to 2417 of the sequence depicted in SEQ ID No: 1.

2. Purified protein obtained by the expression of a modified recombinant DNA sequence wherein said modified sequence comprises codons which are preferred by an organism into which the modified sequence is to be inserted whereby expression in said organism yields protein having the same amino acid sequence as that obtained by the expression of nucleotide sequence 1413 to 2417 of SEQ ID No: 1.

3. Purified protein selected from the group consisting of
   a) the amino acid sequence of SEQ ID No: 2 and,
   b) an amino acid sequence of a mature plant protein which is induced during a hypersensitive response to a plant pathogen wherein said mature plant protein has an amino acid sequence which is at least 80% similar to the sequence of SEQ ID No: 2.

4. A protein according to claim 3 wherein said protein has the amino acid sequence of SEQ ID NO: 2.

5. Purified protein according to claim 2 wherein said organism is a plant.

6. Purified protein according to claim 5 wherein said plant is a corn plant.

7. Purified protein according to claim 5 wherein said plant is a sugar beet plant.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 2778 base pairs
        ( B ) TYPE: nucleic acid
        ( C ) STRANDEDNESS: single
        ( D ) TOPOLOGY: unknown ( i i ) MOLECULE TYPE: genomic DNA ( i i i ) HYPOTHETICAL: NO ( i i i ) ANTI-SENSE: NO ( v i ) ORIGINAL SOURCE:
        ( A ) ORGANISM: Tobacco ( i x ) FEATURE:
    ( A ) NAME/KEY: CDS
    ( B ) LOCATION: 1413..2417

( x i ) SEQUENCE DESCRIPTION: SEQ ID NO: 1:

```
GGATCTTAAT  GTTAGTTTAT  CTCTTGTTTT  GAATATTTGA  TCTTAATTAT  AATTTATCCA      60
CCATAAATTT  TATTTTCAAA  GATCAAACTA  TTGATATGAC  ATTTCACTTT  TTTATCTTTA     120
TGTTTGTAGA  ATCATTAGTG  GTATTGACTC  TTACCAATCA  TTTTTTTTTC  TTTCTCACAC     180
ATTTATATTC  TTAAATTTTC  TTAGTTATTG  TTTAATAATT  GGGTATTTTT  TAATATTACA     240
CGAAAAATTG  ATTAAAAAAA  TATTATTTGA  GTAGAAAAAT  AGTTCAAATA  TAATATAAAC     300
ATATATTATC  GTGGGAGTAT  TTTTTCTCA   ATTCAACTC   TTTATGCAGT  CCACTTAATA     360
TTACTTTTAT  TTTTTCTTGG  TATTAGACAT  TATGGAGTGG  TAATGTATTG  CCAATACGGC     420
TGATTCTTAT  GAAATTGATT  TTATTAAACC  TTCCTACATT  TTTAATAATA  ATTTAATAGA     480
CAAAATTTTA  TTAATTTTAA  ATATTAAATA  TTAAAAATTA  GTAGCATATA  AGGTATTATA     540
GTCCAAAAAA  TAGCTTATTA  CAGTTACGTA  CTCTTCCTAT  GAGTTCTTTC  GTTAATAAT      600
GTAGGGCTAT  TTTGATATAT  TAATATTGTA  TTTATGCTTT  TATAATAATA  TAGGCTCTCT     660
TTTTTCTATA  TGAATTTGGA  CAATATAATA  CATTTTCAAA  TTAAATTAGT  ATCAAATAAT     720
TGTATTTTTG  CTTTTTTAAT  AATTTATACG  CATGAATTTC  ATAATCCAGC  ATATTATGCT     780
AGAACTTTTC  GTGTTTCAAC  TAAAATAATG  ACTATTTTTC  AATGACGTTA  CAAACACTGA     840
CTAATTTTTG  ATTGCAGTCC  GAAAACTATC  TAGTCTATGC  TATTTTCACT  TTTCTAAACT     900
CCCTGCCACT  GTATGCTTTC  ATTGGATTAA  CCTTTAACCA  CACAAATATT  TTAAAGAGTA     960
ATGTTTGACA  GCGTAATTTG  AAACATCTAC  TATGCCTCTG  TATATAATAT  CTAATGTTTG    1020
TTCGTAGACC  AATATTCTAA  TTCCTCTCTT  GTAGACTAAA  CGGGGCTGTA  ACTAACTAAC    1080
CACCATAGTT  ATCTAAATTA  GTGACCCTAG  CGACCATTGA  TAATTTGATA  CTGATCATTG    1140
ACTTCCACCA  AATCTACTTT  CTAAATGTGG  ACTGACTCAT  TATGAATTTG  TGAGGAAAAT    1200
ACTTTCCTAA  TGCTAGTGCT  CTTCCCATTA  TCTAAACTCC  AAAATTTTGT  AAAATTCTTT    1260
GAACCTTCCT  TTAAACTACC  ACAAATTTTC  TTATCCTTTC  CTATCTCACC  ATTATAAATA    1320
GCCACGCACA  TGCAAACCAA  AGGTACACAC  TAAACAAACT  TCATTCTTCA  AATTACTGAT    1380
TACTCGAAAA  AAACACTTCA  AACTTTGCCA  AA ATG GTT CAT GAA AAG CAA GTG         1433
                                     Met Val His Glu Lys Gln Val
                                       1               5
ATA GAG GAA GTA TCC GGC TGG CTT AGA GTT TTC GAA GAC GGT TCA GTA             1481
Ile Glu Glu Val Ser Gly Trp Leu Arg Val Phe Glu Asp Gly Ser Val
         10              15                  20
GAC CGG ACT TGG ACC GGT CCA CCC GAA GTC AAA TTC ATG GCC GAG CCA             1529
Asp Arg Thr Trp Thr Gly Pro Pro Glu Val Lys Phe Met Ala Glu Pro
     25              30                  35
GTC CCA CCC CAT GAC TAC TTC ATC GAC GGC GTT GCC GTC AAA GAT GTA             1577
Val Pro Pro His Asp Tyr Phe Ile Asp Gly Val Ala Val Lys Asp Val
 40              45                  50                          55
GTC GCC GAC GAA AAA TCC GGC AGC CGT CTC CGC ATC TAC TTA CCT GAA             1625
Val Ala Asp Glu Lys Ser Gly Ser Arg Leu Arg Ile Tyr Leu Pro Glu
             60                  65                  70
CGA AAC GAC AAT TCC GCC AGC AAG CTT CCC GTC ATT CTT CAC TTC CAA             1673
Arg Asn Asp Asn Ser Ala Ser Lys Leu Pro Val Ile Leu His Phe Gln
             75                  80                  85
GGC GGC GGC TTT TGT GTC AGC CAT GCT GAT TGG TTC ATG TAC TAC ACT             1721
Gly Gly Gly Phe Cys Val Ser His Ala Asp Trp Phe Met Tyr Tyr Thr
         90                  95                  100
```

```
GTC  TAC  ACG  CGC  CTA  GCG  CGC  GCG  GCC  AAA  GCT  ATC  ATT  GTC  TCC  GTC    1769
Val  Tyr  Thr  Arg  Leu  Ala  Arg  Ala  Ala  Lys  Ala  Ile  Ile  Val  Ser  Val
     105                 110                      115

TTC  CTC  CCC  CTC  GCG  CCG  GAG  CAC  CGC  CTC  CCA  GCT  GCC  TGC  GAT  GCC    1817
Phe  Leu  Pro  Leu  Ala  Pro  Glu  His  Arg  Leu  Pro  Ala  Ala  Cys  Asp  Ala
120                      125                      130                      135

GGT  TTC  GCC  GCT  CTC  CTC  TGG  CTC  CGG  GAC  CTC  TCC  CGG  CAG  CAA  GGA    1865
Gly  Phe  Ala  Ala  Leu  Leu  Trp  Leu  Arg  Asp  Leu  Ser  Arg  Gln  Gln  Gly
                    140                 145                      150

CAC  GAG  CCC  TGG  CTC  AAC  GAT  TAC  GCA  GAT  TTC  AAC  CGA  GTA  TTC  CTC    1913
His  Glu  Pro  Trp  Leu  Asn  Asp  Tyr  Ala  Asp  Phe  Asn  Arg  Val  Phe  Leu
               155                 160                      165

ATC  GGA  GAC  AGC  TCC  GGC  GGG  AAC  ATA  GTC  CAC  CAA  GTT  GCC  GTC  AAA    1961
Ile  Gly  Asp  Ser  Ser  Gly  Gly  Asn  Ile  Val  His  Gln  Val  Ala  Val  Lys
          170                      175                      180

GCC  GGC  GAG  GAA  AAC  TTA  TCT  CCA  ATG  CGA  CTG  GCC  GGC  GCA  ATT  CCG    2009
Ala  Gly  Glu  Glu  Asn  Leu  Ser  Pro  Met  Arg  Leu  Ala  Gly  Ala  Ile  Pro
     185                      190                      195

ATC  CAT  CCA  GGT  TTC  GTG  CGG  TCC  TAT  CGG  AGC  AAA  TCG  GAG  CTA  GAA    2057
Ile  His  Pro  Gly  Phe  Val  Arg  Ser  Tyr  Arg  Ser  Lys  Ser  Glu  Leu  Glu
200                 205                      210                           215

CAA  GAG  CAA  ACC  CCG  TTT  TTA  ACA  TTA  GAT  ATG  GTG  GAT  AAA  TTT  CTA    2105
Gln  Glu  Gln  Thr  Pro  Phe  Leu  Thr  Leu  Asp  Met  Val  Asp  Lys  Phe  Leu
                    220                      225                      230

GGG  TTA  GCT  TTA  CCA  GTA  GGG  AGC  AAC  AAG  GAT  CAT  CAA  ATA  ACA  TGT    2153
Gly  Leu  Ala  Leu  Pro  Val  Gly  Ser  Asn  Lys  Asp  His  Gln  Ile  Thr  Cys
                    235                      240                      245

CCG  ATG  GGA  GAG  GCG  GCG  CCG  GCA  GTG  GAG  GAG  CTT  AAA  TTA  CCG  CCT    2201
Pro  Met  Gly  Glu  Ala  Ala  Pro  Ala  Val  Glu  Glu  Leu  Lys  Leu  Pro  Pro
          250                      255                      260

TAT  TTG  TAC  TGT  GTG  GCG  GAG  AAA  GAT  CTG  ATA  AAG  GAC  ACT  GAA  ATG    2249
Tyr  Leu  Tyr  Cys  Val  Ala  Glu  Lys  Asp  Leu  Ile  Lys  Asp  Thr  Glu  Met
     265                      270                      275

GAG  TTT  TAC  GAA  GCT  ATG  AAA  AAG  GGG  GAA  AAG  GAT  GTA  GAG  CTG  TTT    2297
Glu  Phe  Tyr  Glu  Ala  Met  Lys  Lys  Gly  Glu  Lys  Asp  Val  Glu  Leu  Phe
280                      285                      290                      295

ATT  AAC  AAT  GGA  GTG  GGA  CAT  AGC  TTT  TAT  CTT  AAC  AAA  ATT  GCT  GTT    2345
Ile  Asn  Asn  Gly  Val  Gly  His  Ser  Phe  Tyr  Leu  Asn  Lys  Ile  Ala  Val
               300                      305                      310

AGA  ATG  GAC  CCT  GTA  ACT  GGT  TCT  GAA  ACT  GAA  AAA  CTT  TAT  GAA  GCC    2393
Arg  Met  Asp  Pro  Val  Thr  Gly  Ser  Glu  Thr  Glu  Lys  Leu  Tyr  Glu  Ala
               315                      320                      325

GTT  GCA  GAG  TTC  ATC  AAC  AAG  CAT  TA  AAAGGAGAAA  ATTTGTGGTT                 2439
Val  Ala  Glu  Phe  Ile  Asn  Lys  His
          330                      335

TTGCAGAATA  TTTGTTGTT  GCATGCATGT  TCAAGATTTT  GATGTACCGT  CTTGATTGTC              2499

ACGTTCTAAT  GGTTTTGTAA  TTATAATTAT  GAGGAGTAAA  TTTCTATTGT  TGCGTAGAAA             2559

TGTTTTTTCT  TTGGTAGTAA  ATGTTTATTT  GTAATACTTT  AAAAAGTGGA  CAAATTTCTT             2619

TTGAGATTCA  TGAAATAATA  TCTTTAAATT  TCGAATGTCA  ATAAGTCCAG  AAATTGAAAT             2679

GTATCTGTAC  CGTCAATGAA  GTCTCCTTGA  GGCTTTTTTT  CACATGATAT  CGTCTATACC             2739

ACCAAAAAGT  TTGATAAGCT  ATACAATATG  AGATTCTCG                                      2778
```

( 2 ) INFORMATION FOR SEQ ID NO: 2:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| Met | Val | His | Glu | Lys | Gln | Val | Ile | Glu | Glu | Val | Ser | Gly | Trp | Leu | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | Phe | Glu | Asp | Gly | Ser | Val | Asp | Arg | Thr | Trp | Thr | Gly | Pro | Pro | Glu |
|     |     |     | 20  |     |     |     |     | 25  |     |     |     |     | 30  |     |     |
| Val | Lys | Phe | Met | Ala | Glu | Pro | Val | Pro | Pro | His | Asp | Tyr | Phe | Ile | Asp |
|     |     | 35  |     |     |     |     | 40  |     |     |     |     |     | 45  |     |     |
| Gly | Val | Ala | Val | Lys | Asp | Val | Val | Ala | Asp | Glu | Lys | Ser | Gly | Ser | Arg |
|     | 50  |     |     |     |     | 55  |     |     |     |     | 60  |     |     |     |     |
| Leu | Arg | Ile | Tyr | Leu | Pro | Glu | Arg | Asn | Asp | Asn | Ser | Ala | Ser | Lys | Leu |
| 65  |     |     |     |     | 70  |     |     |     |     | 75  |     |     |     |     | 80  |
| Pro | Val | Ile | Leu | His | Phe | Gln | Gly | Gly | Gly | Phe | Cys | Val | Ser | His | Ala |
|     |     |     |     | 85  |     |     |     |     | 90  |     |     |     |     | 95  |     |
| Asp | Trp | Phe | Met | Tyr | Tyr | Thr | Val | Tyr | Thr | Arg | Leu | Ala | Arg | Ala | Ala |
|     |     |     | 100 |     |     |     |     | 105 |     |     |     |     | 110 |     |     |
| Lys | Ala | Ile | Ile | Val | Ser | Val | Phe | Leu | Pro | Leu | Ala | Pro | Glu | His | Arg |
|     |     | 115 |     |     |     |     | 120 |     |     |     |     |     | 125 |     |     |
| Leu | Pro | Ala | Ala | Cys | Asp | Ala | Gly | Phe | Ala | Ala | Leu | Leu | Trp | Leu | Arg |
|     | 130 |     |     |     |     | 135 |     |     |     |     | 140 |     |     |     |     |
| Asp | Leu | Ser | Arg | Gln | Gln | Gly | His | Glu | Pro | Trp | Leu | Asn | Asp | Tyr | Ala |
| 145 |     |     |     |     | 150 |     |     |     |     | 155 |     |     |     |     | 160 |
| Asp | Phe | Asn | Arg | Val | Phe | Leu | Ile | Gly | Asp | Ser | Ser | Gly | Gly | Asn | Ile |
|     |     |     |     | 165 |     |     |     |     | 170 |     |     |     |     | 175 |     |
| Val | His | Gln | Val | Ala | Val | Lys | Ala | Gly | Glu | Glu | Asn | Leu | Ser | Pro | Met |
|     |     |     | 180 |     |     |     |     | 185 |     |     |     |     | 190 |     |     |
| Arg | Leu | Ala | Gly | Ala | Ile | Pro | Ile | His | Pro | Gly | Phe | Val | Arg | Ser | Tyr |
|     |     | 195 |     |     |     |     | 200 |     |     |     |     | 205 |     |     |     |
| Arg | Ser | Lys | Ser | Glu | Leu | Glu | Gln | Glu | Gln | Thr | Pro | Phe | Leu | Thr | Leu |
|     | 210 |     |     |     |     | 215 |     |     |     |     | 220 |     |     |     |     |
| Asp | Met | Val | Asp | Lys | Phe | Leu | Gly | Leu | Ala | Leu | Pro | Val | Gly | Ser | Asn |
| 225 |     |     |     |     | 230 |     |     |     |     | 235 |     |     |     |     | 240 |
| Lys | Asp | His | Gln | Ile | Thr | Cys | Pro | Met | Gly | Glu | Ala | Ala | Pro | Ala | Val |
|     |     |     |     | 245 |     |     |     |     | 250 |     |     |     |     | 255 |     |
| Glu | Glu | Leu | Lys | Leu | Pro | Pro | Tyr | Leu | Tyr | Cys | Val | Ala | Glu | Lys | Asp |
|     |     |     | 260 |     |     |     |     | 265 |     |     |     |     | 270 |     |     |
| Leu | Ile | Lys | Asp | Thr | Glu | Met | Glu | Phe | Tyr | Glu | Ala | Met | Lys | Lys | Gly |
|     |     | 275 |     |     |     |     | 280 |     |     |     |     | 285 |     |     |     |
| Glu | Lys | Asp | Val | Glu | Leu | Phe | Ile | Asn | Asn | Gly | Val | Gly | His | Ser | Phe |
|     | 290 |     |     |     |     | 295 |     |     |     |     | 300 |     |     |     |     |
| Tyr | Leu | Asn | Lys | Ile | Ala | Val | Arg | Met | Asp | Pro | Val | Thr | Gly | Ser | Glu |
| 305 |     |     |     |     | 310 |     |     |     |     | 315 |     |     |     |     | 320 |
| Thr | Glu | Lys | Leu | Tyr | Glu | Ala | Val | Ala | Glu | Phe | Ile | Asn | Lys | His |     |
|     |     |     |     | 325 |     |     |     |     | 330 |     |     |     |     | 335 |     |

( 2 ) INFORMATION FOR SEQ ID NO: 3:

( i ) SEQUENCE CHARACTERISTICS:
  ( A ) LENGTH: 93 base pairs
  ( B ) TYPE: nucleic acid
  ( C ) STRANDEDNESS: single
  ( D ) TOPOLOGY: unknown ( i i ) MOLECULE TYPE: genomic DNA ( i i i ) HYPOTHETICAL: NO (iii) ANTI-SENSE: NO (xi) SEQUENCE DESCRIPTION: SEQ ID NO: 3:

```
TTTGCCAAAA TGGTTCATGA AAAGCAAGTG ATAGAGGAAG TATCCGGCTG GCTTAGAGTT    60
TTCGGGGTAG GTCAGTCCCT TATGTTACGT CCT                                93
```